US007122002B2

(12) United States Patent
Okada

(10) Patent No.: US 7,122,002 B2
(45) Date of Patent: Oct. 17, 2006

(54) ENDOSCOPE HOOD AND ENDOSCOPIC MUCOSA CUTTING DEVICE

(75) Inventor: Tsutomu Okada, Tokyo (JP)

(73) Assignee: Olympus Corporation, Tokyo (JP)

( * ) Notice: Subject to any disclaimer, the term of this patent is extended or adjusted under 35 U.S.C. 154(b) by 19 days.

(21) Appl. No.: 10/910,671

(22) Filed: Aug. 3, 2004

(65) Prior Publication Data

US 2005/0033115 A1 Feb. 10, 2005

(30) Foreign Application Priority Data

Aug. 8, 2003 (JP) ........................... P2003-290284

(51) Int. Cl.
*A61B 1/00* (2006.01)

(52) U.S. Cl. ...................... 600/127; 600/104; 600/105; 600/106; 600/107; 600/164; 606/46; 606/47; 606/170

(58) Field of Classification Search ........ 600/104–107, 600/127; 606/46, 47, 170
See application file for complete search history.

(56) References Cited

U.S. PATENT DOCUMENTS 6,059,719 A * 5/2000 Yamamoto et al. ......... 600/127
6,306,081 B1 * 10/2001 Ishikawa et al. ............ 600/127
6,524,234 B1 * 2/2003 Ouchi ........................ 600/127
6,916,284 B1 * 7/2005 Moriyama .................. 600/127
2001/0053909 A1 * 12/2001 Nakada et al. ................ 606/47

* cited by examiner

*Primary Examiner*—Linda C. M. Dvorak
*Assistant Examiner*—Matthew J. Kasztejna
(74) *Attorney, Agent, or Firm*—Scully, Scott, Murphy & Presser, P.C.

(57) ABSTRACT

An endoscope hood comprises a cap section which has A cap section which has a nail section inside of an inner surface of a tip margin, an attaching section which is disposed to a base terminal of the cap section to be attached to a tip of an inserting section of the endoscope, a soft tube 16 of which tip aperture connects to an inside of the cap section so as to insert the snare sheath therethrough, a snare wire which is inserted in the cap section via the soft tube 16, and a snare wire feeding section which is formed by making a notch section in a part of the soft tube in the nail section in a corresponding position to the tip aperture, such that the snare wire can be spread in the cap section so as to be disposed inside of the nail section, and the center axis of the soft tube is disposed so as to pass through a range of the snare wire feeding section. By doing this, it is possible to provide an endoscope hood and an endoscopic mucosa cutting device having therefore in which it is possible to dispose a loop of the snare wire in an area which is inside of the nail section of the cap section reliably.

5 Claims, 7 Drawing Sheets

ENDOSCOPE HOOD AND ENDOSCOPIC MUCOSA CUTTING DEVICE

The present application is based on patent application No. 2003-290284 filed Aug. 8, 2003 in Japan, the content of which is incorporated herein by reference.

BACKGROUND OF THE INVENTION

1. Field of the Invention

The present invention relates to an endoscope hood and a endoscopic mucosa cutting device which are used to be inserted in a live organization together with a high frequency snare for a medical operation such as a demucosation for a live organization by conducting a high frequency electric current.

2. Description of Related Art

In recent years, endoscopic demucosations are performed for cutting a mucosa in a ailing section without performing an abdominal operation but using an endoscope instead. An endoscopic demucosation which used a high frequency snare is know for such a methods.

For such an endoscopic demucosation, an endoscope hood is proposed which is used in an auxiliary manner so as to be attached to a tip of an inserting section of the endoscope (See Japanese Unexamined Utility Application, First Publication No. Hei 6-75402, pages 4 to 5, FIG. 1, and Japanese Unexamined Patent Application, First Publications No. 2001-275933, pages 2 to 4, and FIG. 1). In such a case, a nail section which protrudes toward an inside of an tip margin of an approximate cylindrical cap section which is formed by a transparent member in a flange manner is provided so as to be used while being attached to the tip of the inserting section of the endoscope. The mucosa is cut by disposing the snare wire of the high frequency snare which is conducted via a channel in the endoscope over an inner section of the nail section, by absorbing the mucosa in the cap, and grabbing the mucosa by a loop wire of the high frequency snare, and conducting an electricity to the high frequency snare.

Also, an endoscope hood is proposed which can be used compatibly with an ultra-sonic probe which is inserted in the channel of the endoscope by connecting the tip of the soft tube to a connecting port which is disposed in the cap section and inserting the sheath of the high frequency snare via the soft tube (See pages 2 to 5, and FIG. 1 in a Japanese Unexamined Patent Application, First Publication No. 2002-45369).

SUMMARY OF THE INVENTION

An object of the present invention is to provide an endoscope hood and an endoscopic mucosa cutting device having therefore such that the loop of the snare wire is disposed in the inner portion of the nail section of the cap section reliably for performing the endoscopic demucosation.

Following structures are employed for solving the above problems. That is, an endoscope hood of the present invention comprises an approximate cylindrical cap section which has a flange section which protrudes toward an inside of an inner surface of a tip margin, an attaching section which is disposed to a base terminal of the cap section to be attached to a tip of an inserting section of the endoscope, a soft tube which is disposed outside of the inserting section of the endoscope when the cap section is attached to the endoscope for inserting snare sheath of high frequency snare such that an aperture of the tip is connected to the inside of the cap section, a high frequency snare which is inserted in the cap section via the soft tube, a snare wire feeding section in which a notch is formed in a part of the snare wire feeding section in a corresponding position to the aperture of the tip of the soft tube in the flange section such that the snare wire of the high frequency snare can be disposed inside of the flange section by spreading the snare wire of the high frequency snare in the cap section, and a center axis of the soft tube is disposed in a position which passes through a scope of the snare wire feeding section.

Also, an endoscope hood of the present invention comprises an approximate cylindrical cap section which has a flange section which protrudes toward an inside of an inner surface of a tip margin, an attaching section which is disposed to a base terminal of the cap section to be attached to a tip of an inserting section of the endoscope, a soft tube for inserting snare sheath of high frequency snare into the soft tube which is disposed outside of the inserting section of the endoscope when the cap section is attached to the endoscope for inserting snare sheath of high frequency snare such that an aperture of the tip is connected to the inside of the cap section, a high frequency snare which is inserted in the cap section via the soft tube, a snare wire feeding section in which a notch is formed in a part of the snare wire feeding section in a corresponding position to the aperture of the tip of the soft tube in the flange section such that the snare wire of the high frequency snare can be disposed inside of the flange section by spreading the snare wire of the high frequency snare in the cap section, and, a center axis of the snare sheath which is inserted in the aperture of the tip of the soft tube is disposed in a position which passes through a scope of the snare wire feeding section.

According to this invention, the snare sheath is inserted into the soft tube such that the center axis of the snare sheath passes through the snare feeding section when the snare wire is disposed in an inner portion of the flange section by feeding the snare wire from the snare sheath. Therefore, it is possible to dispose a portion of the snare wire near the snare sheath in an inner section of the flange section reliably; thus, it is possible to restrict that the snare wire is removed from the flange section even if the cap section receives a force externally.

Also, the endoscopic mucosa cutting device according to the present invention comprises the endoscope hood and the high frequency snare.

BRIEF DESCRIPTION OF THE DRAWINGS

FIG. 1A is a view for a general structure. FIG. 1B is a plan view for showing a fixing section.

FIG. 2A is an isometric view. FIG. 2B is a view for showing important sections shown in FIG. 2A.

FIG. 3A is a cross section viewed in an axial direction. FIG. 3B is a view for showing important sections shown in FIG. 3A.

DETAILED DESCRIPTION OF THE INVENTION

Hereinafter, a first embodiment of the endoscopic mucosa cutting device is explained with reference to FIGS. 1A to 4.

Figure 1B:
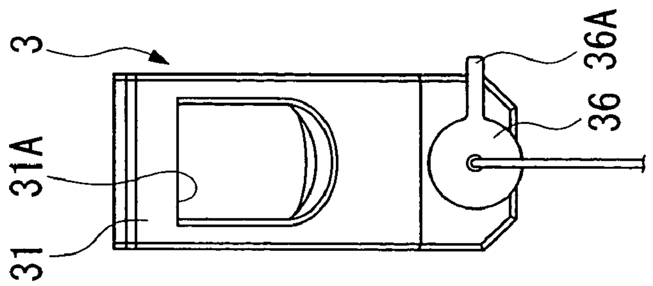
FIGS. 1A and 1B show an endoscopic mucosa cutting device according to a first embodiment of the present invention.
Figure 1A:
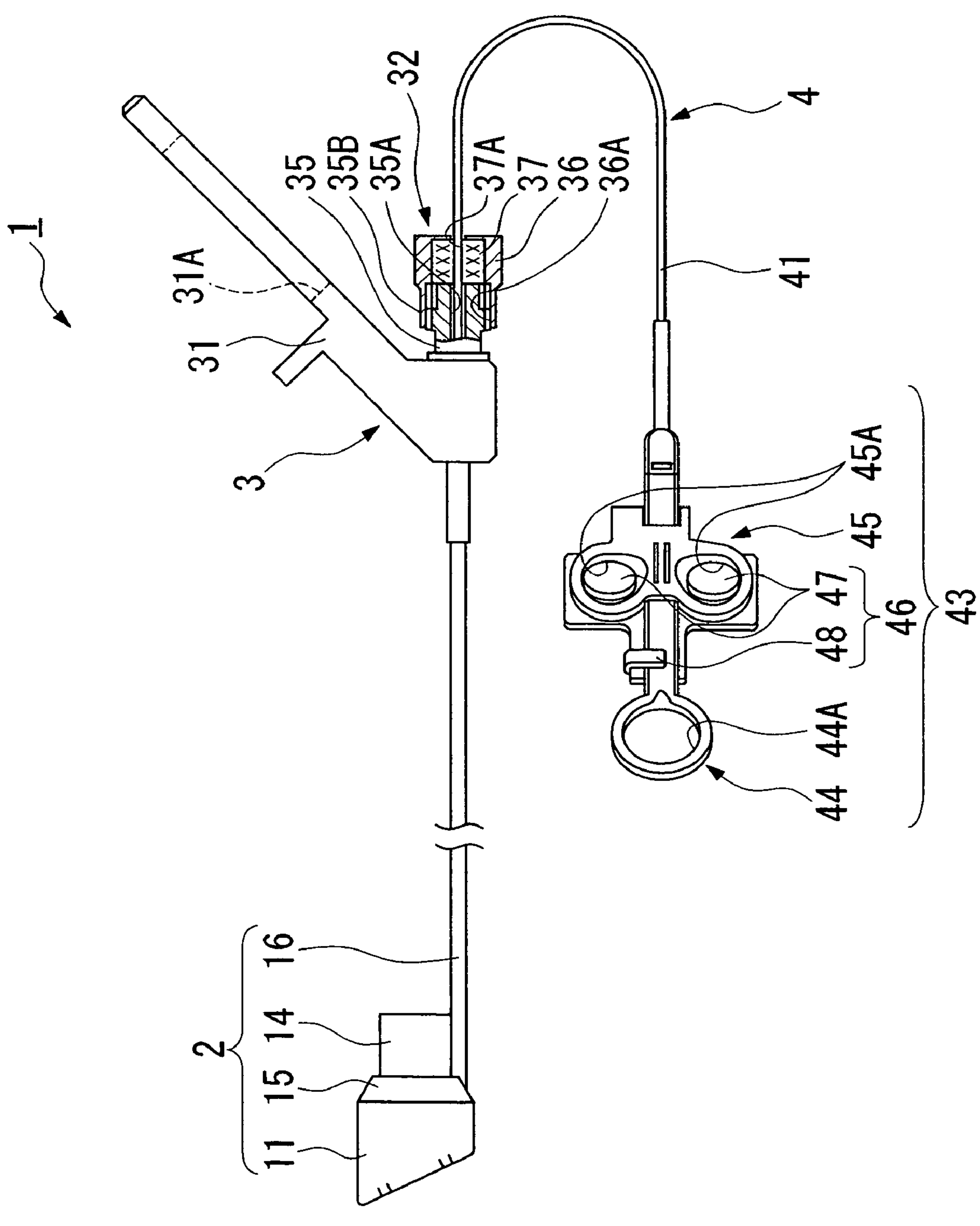
Figure 2A:
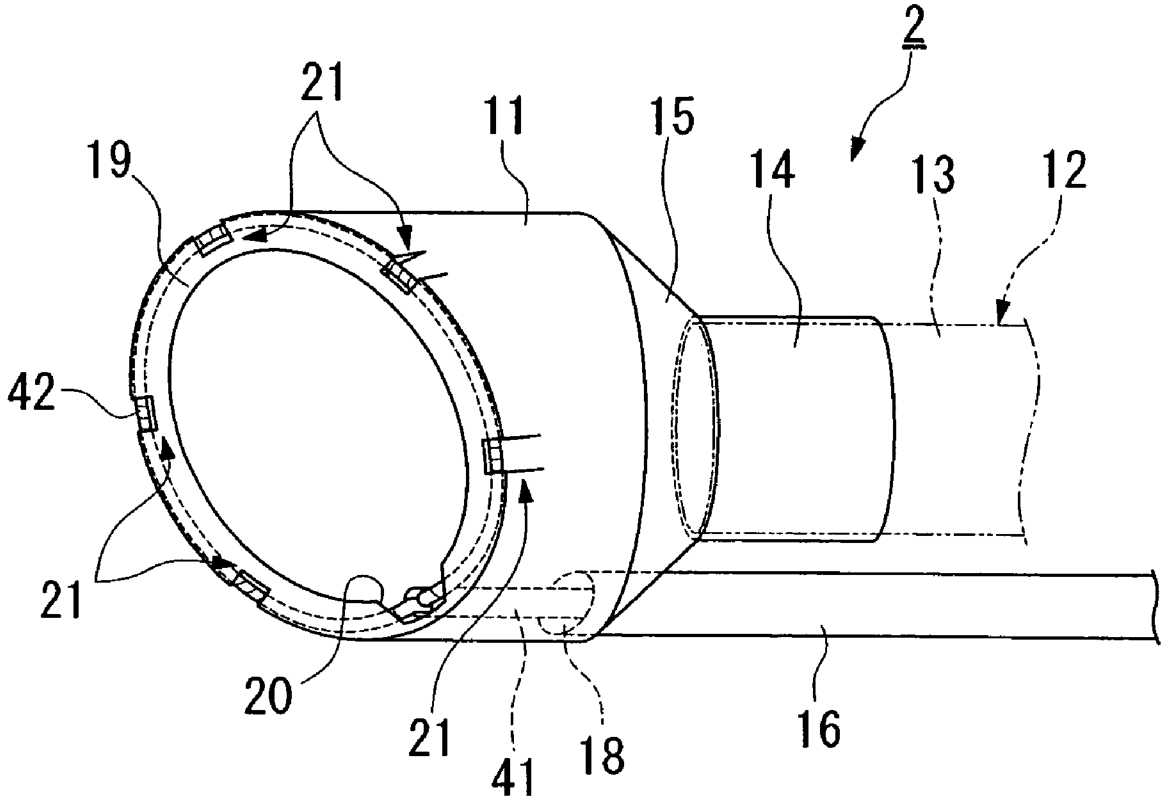
FIGS. 2A and 2B are views for showing an endoscope hood according to the first embodiment of the present invention.
Figure 2B:
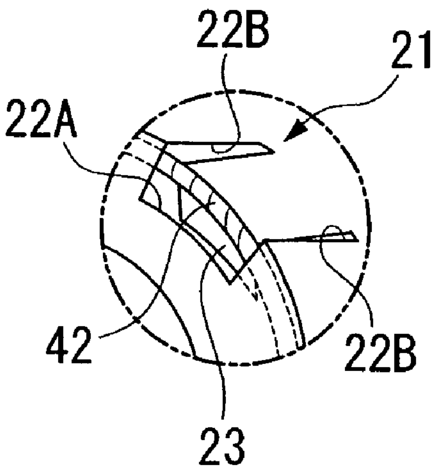
Figure 3A:
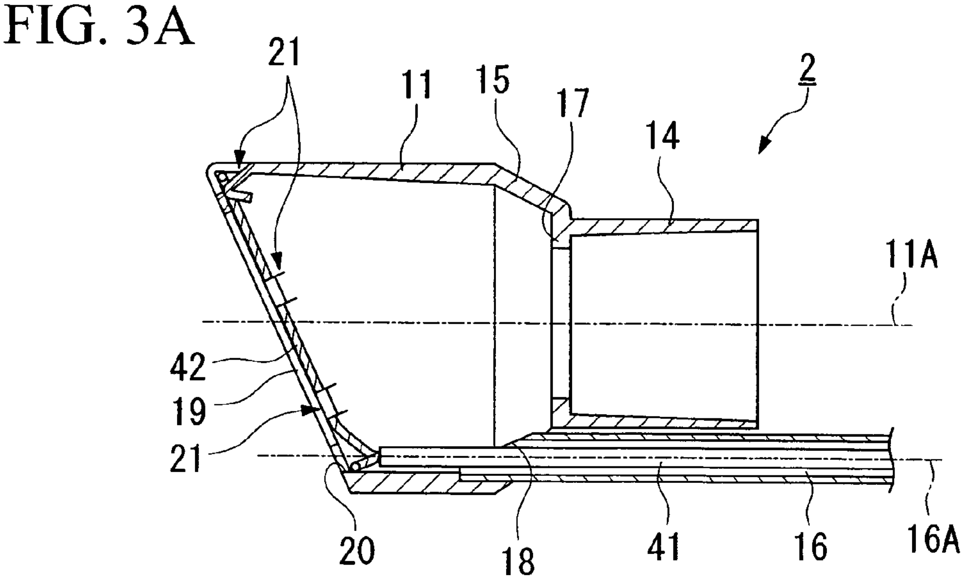
FIGS. 3A and 3B are views for showing an endoscope hood according to the first embodiment of the present invention.
Figure 3B:
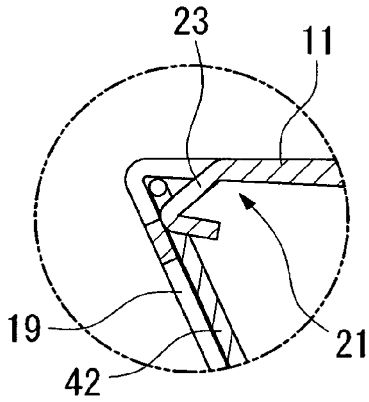
Figure 4:
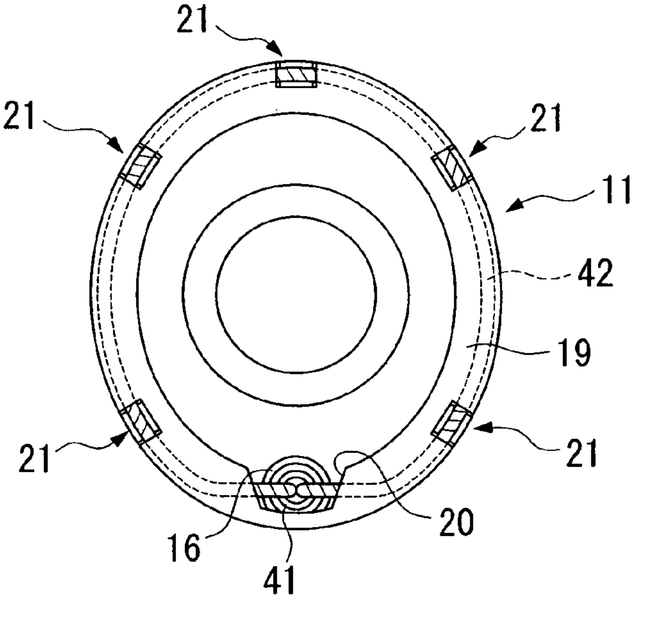
FIG. 4 is a plan view for showing a tip of a cap section in an endoscope hood according to the first embodiment of the present invention.

As shown in FIGS. 1A and 1B, the endoscopic mucosa cutting device according to the present embodiment comprises and endoscope hood 2, a fixing section which is disposed near the base terminal of the endoscope hood 2, and a high frequency snare section 4.

As shown in FIGS. 1A to 4, the endoscope hood 2 is formed by a transparent member. The endoscope hood 2 comprises an approximate cylindrical cap section 11, an approximate cylindrical attaching section 14 which is detachably attached to the tip section of the inserting section 13 of the endoscope 12 which is inserted in a live organization, a gap section 15 which is formed in a taper manner which is connected to the base terminal section and the attaching section 14 of the cap section, and a soft tube 16 which is connected to the gap section 15.

A diameter of an aperture of the cap section 11 is larger than a diameter of an aperture of the attaching section 14 such that the tip section of the cap section 11 is formed in a slanted manner with reference to an axial direction of the cap section 11.

An inner diameter of the attaching section 14 is approximately the same as an outer diameter of the inserting section 13. An endoscope stopping section 17 which protrudes to inside of an inner surface in a flange manner is disposed in the attaching section 14 such that a diameter of an aperture of the tip is smaller than the outer diameter of the tip section of the inserting section 13.

A connecting port 18 which connects to the inside of the cap section 11 is formed in the gap section 15 such that a tip section of the soft tube 16 is connected thereto. Here, the tip section of the soft tube 16 is fixed to the cap section 11 in an air-tight manner by various methods such as a bonding method or melt-bonding method.

Here, a center axis 16A of the soft tube is connected to a center axis 11*a* of the cap section 11 in an approximate parallel manner.

A nail section (flange section) 19 which protrudes toward an inside of the inner surface with a constant width is disposed in the tip section of the cap section 11.

The nail section 19 comprises a snare wire feeding section 20 which is an area which is formed by making a notch section in a part of the nail section 19 and flexible stopping sections 21 which are formed in appropriate intervals in a circumferential direction.

The snare wire feeding section 20 is formed by making a notch section in the nail section 19 in a corresponding position to the tip aperture of the soft tube 16 such that the center axis 16A of the soft tube 16 passes through in a range of the snare wire feeding section 20.

The flexible stopping section 21 is formed by bending a stopping plate 23 which is formed by a slit 22A which is formed in an approximate center of the nail section 19 in a circumferential direction toward an inside of the circumferential direction and two slits 22B which are formed in an approximate parallel manner in a center axis direction over an outer wall of the cap section 11 with an appropriate width from both ends of the slit 22A.

As shown in FIGS. 1A and 1B, the base terminal of the soft tube 16 is connected to the fixing section 3 which fixes the sheath releasably and fixes the soft tube 16 to the endoscope 12.

The fixing section 3 is provided with a hook 31 for fixing the endoscope 12 and a sheath fixing section 32.

A hole section 31A is formed in the hook 31. The hole section 31A has a connecting port (not shown in the drawing) which connects to the soft tube 16 and the sheath fixing section 32 near the base terminal.

Also, the sheath fixing section 32 is formed by a base section 35 which has a through hole 35A which connects to the inside of the soft tube 16 and a male thread 35B, a rotative ring 36 which has a female thread 36A which engages the male thread 35B, and a flexible tube 37 which is contained in the base section 35 and the rotative ring 36 by engaging the male thread 35B and the rotative ring 36 such that the flexible tube 37 has the through hole 37A.

A high frequency snare section 4 is inserted in the soft tube 16.

As shown in FIGS. 1A to 4, the high frequency snare section 4 has a sheath (snare sheath) 32 which has a flexibility so as to be inserted into the soft tube 16, an approximate ring snare wire 42 which protrudes from the tip of the sheath 41, an operating section 43 for operating a length of the snare wire 42 which protrudes from the tip of the sheath 41 in a base terminal of the sheath 41, and an operating wire (drawing is omitted) which is inserted in the sheath 41 and connects the snare wire 42 and the operating section 43.

The sheath 41 is inserted into the soft tube 16, a through hole 35A, and the flexible tube 37 and fixed in the through hole 37A of the flexible tube 37. The through hole 37A of the built-in flexible tube 37 is released by rotating the knob 36A which is disposed on the rotative ring 36; thus, the sheath 41 can be fed forwardly and backwardly.

As shown in FIGS. 2A to 4, the snare wire 42 is disposed in a predetermined position by the nail section 19 and the stopping plate 23 alternately by feeding the snare wire 42 to the snare wire feeding section 20 of the cap section 11 from the tip of the sheath 41 along the nail section 19 of the cap section 11 so as to be engaged in the inside of the nail section 19.

The operating section 43 is provided with a main body 44, a slider 45 which is disposed so as to move freely in a forward direction and a backward direction with reference to the main body 44 such that an end section of an operating wire is connected thereto, and a regulating member 46 which regulates the movement of the slider in the forward direction and the backward direction.

A finger hole section 44A is disposed in the main body 44 for disposing a finger of an operator during the operation. Also, a similar finger hole section 45A is disposed in the slider 45.

A convex section 47 which engages the finger hole section 45A of the slider 45 and a fixing section 48 which is fixed on the main body 44 are disposed on the regulating member 46; thus, the movement of the slider is regulated in the forward direction and the backward direction.

A method for cutting the mucosa A1 by using the endoscopic mucosa cutting device 1 which has the above explained structure is explained with reference to FIGS. 5A to 5C.

Figures 5A, 5B, 5C:
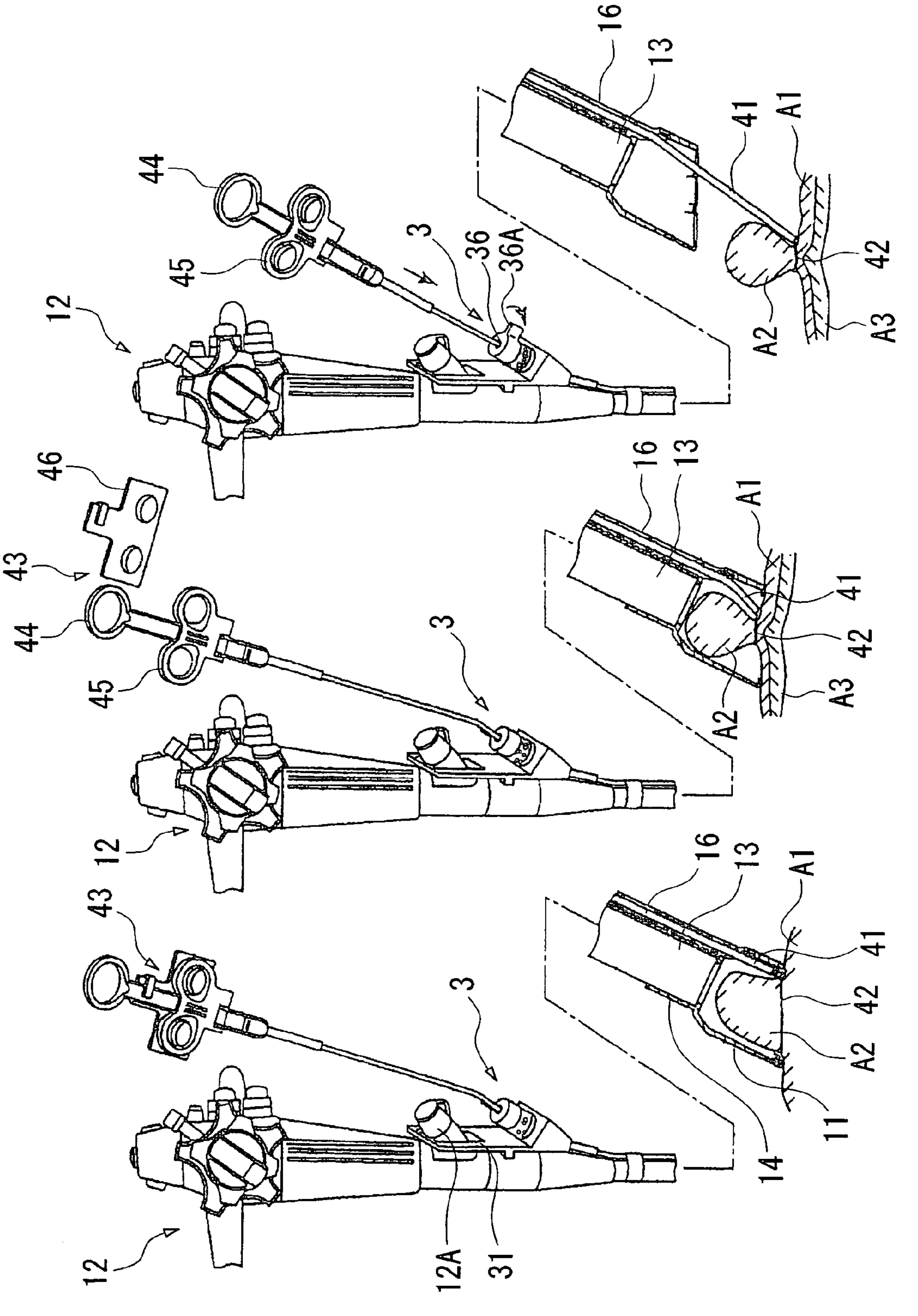
FIGS. 5A to 5C are views for showing a method for cutting a mucosa by using the endoscope hood according to the first embodiment of the present invention.

First, as shown in FIG. 5A, the tip section of the inserting section 13 of the endoscope 12 is attached to the attaching section 14; thus, the soft tube 16 is fixed by a member such as a medical tape along the inserting section 13 of the endoscope 12. Consequently, the hook 31 is hooked near a forceps cap 12A of the endoscope 12 so as to be fixed thereon.

The endoscope 12 and the endoscope hood 2 are inserted in the live organization under such a condition; thus, a tip aperture of the cap section 11 is moved toward a section in which a mucosa should be cut. Consequently, an aperture of the tip of the cap section 11 is compressed to the mucosa A1. Under such a condition, the mucosa A1 is attracted into the inside of the cap section 11 by a negative pressure; thus, a section A2 which is cut from the mucosa A1 protrudes because it is absorbed by an absorbing device (drawing is omitted) via a channel of the endoscope 12.

Next, as shown in FIG. 5B, the regulating member 46 is removed from the operating section 43 of the high frequency snare section 4 and the slider 45 is retracted with reference to the main body 44. Thus, the snare wire 42 is hooked off from the flexible stopping section 21 so as to be attracted in the sheath 41; thus, a root section of the section A2 which is cut from the mucosa A1 is bound.

Next, as shown in FIG. 5C, the through hole 37A of the flexible tube 37 is released by rotating the rotative ring 36 by supporting the knob 36A of the fixing section 3 such that the sheath 41 can be moved in a forward direction and a backward direction; thus, the sheath 41 is compressed into the soft tube 16. In such a case, the tip of the sheath 41 protrudes from the cap section 11; therefore the section A2 which is cut and binded by the snare wire 42 protrudes from inside of the cap section 11.

After that, the condition of a mucosa A1 and a muscularis A3 are inspected by using an ultra-sonic probe which is inserted in the channel of the endoscope 12 so as to confirm that the muscularis A3 is not rolled therein.

Consequently, a high frequency electric current is applied to the snare wire 42 so as to cut the mucosa A1 while drawing and squeezing the area which is supposed to be cut therefrom. The mucosa A1 which is cut therefrom is absorbed in the channel after devices such as an ultra-sonic probe are the mucosa A1 is extracted from the channel of the endoscope 12 so as to be extracted out of the live organization together with the endoscope 12 under condition that it is maintained in the cap section 11 so as to be collected.

In the endoscopic mucosa cutting device 1 according to the present embodiment, the center axis 16A of the soft tube 16 is disposed in a position such that a center axis of the sheath 41 of the high frequency snare section 4 which is inserted into the tip aperture of the soft tube 16 should pass through a range of the snare wire feeding section 20; therefore, a section near the sheath 41 of the snare wire 42 is engaged to an inside of the snare section 19 reliably when the snare wire 42 is disposed inside of the nail section 19. Also, the flexible stopping section 21 is formed in the nail section 19; therefore, the snare wire 42 is disposed in a section inside of the nail section 19 more reliably. Therefore, it is possible to restrict a possibility that the snare wire 42 is removed off from the cap section 11 when it is inserted in the live organization and a force is applied to the cap section 11 in the live organization; thus, the cap section 11 is deformed.

Here, although the sheath 41 of the high frequency snare 3 is inserted in the soft tube 16 in the endoscopic mucosa cutting device 1 such that the snare wire 42 is engaged in an inner section of the nail section 19 in advance, it is acceptable if the sheath 41 is inserted in the soft tube 16 before the sheath 41 is inserted in the live organization so as to engage the snare wire 42 thereto. In such a case, the forward movement and the backward movement of the sheath 41 is stopped by rotating the knob 36A of the rotative ring 36 so as to contract the through hole 37A of the flexible tube 37 after inserting the sheath 41 in the soft tube 16 via the fixing section 3.

Figure 6:
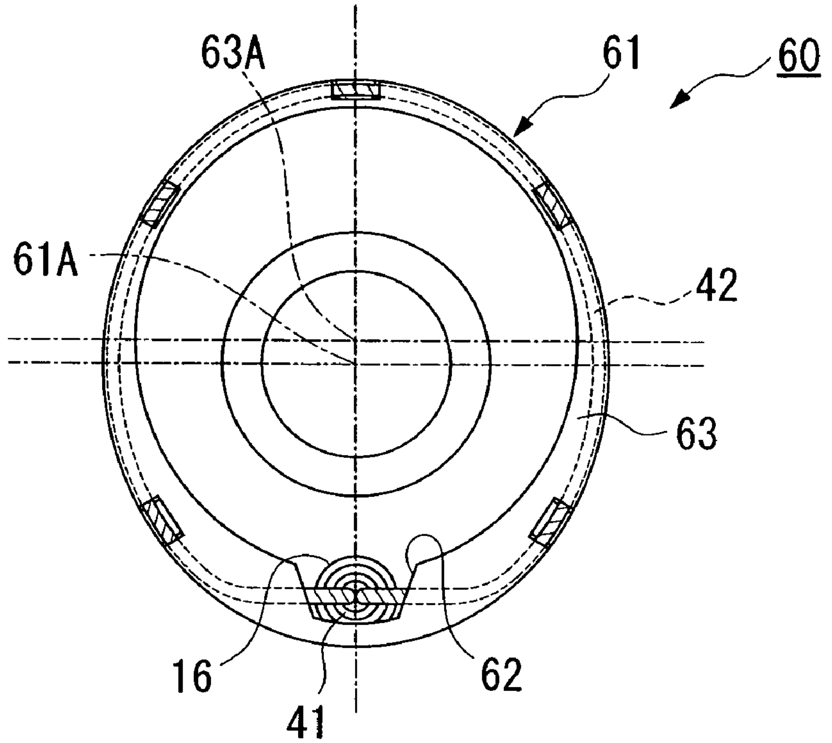
FIG. 6 is a plan view for showing a tip of a cap section in an endoscope hood according to a second embodiment of the present invention.

Next, a second embodiment is explained with reference to FIG. 6.

Here, a basic structure in the present embodiment which is explained here is similar to the basic structure in the above explained first embodiment. In the present embodiment, other feature is added to the above explained first embodiment. Therefore, the same reference numeral are added to FIG. 6 as the reference numeral in FIG. 3 so as to omit the explanation therefor.

The second embodiment is different from the first embodiment in that a width of the nail section 19 in the first embodiment is formed equally and the cap section 61 in the endoscope hood 60 in the second embodiment has a nail section 63 of which width increases toward a snare wire feeding section 62. That is, as shown in FIG. 6, an aperture center 63A which is formed by the nail section 63 is formed so as to be disposed farther from the snare wire feeding section 62 than a center axis 61A of the cap section 61.

The endoscope hood 60 has a similar operability and an effect which are equal to those in the endoscope hood 2 in the first embodiment. If a range of the snare wire feeding section 62 is formed larger and the center of the soft tube 16 is disposed more separately from an inner margin of the nail section 63 in an outer circumferential direction, it is possible to engage a section near the sheath 41 of the snare wire 42 in an inside of the nail section 63 more reliably.

Next, a third embodiment is explained with reference to FIG. 7.

Here, a basic structure in the present embodiment which is explained here is similar to the basic structure in the above explained first embodiment. In the present embodiment, other feature is added to the above explained first embodiment. Therefore, the same reference numeral are added to FIG. 7 as the reference numeral in FIG. 2A so as to omit the explanation therefor.

Figure 7:
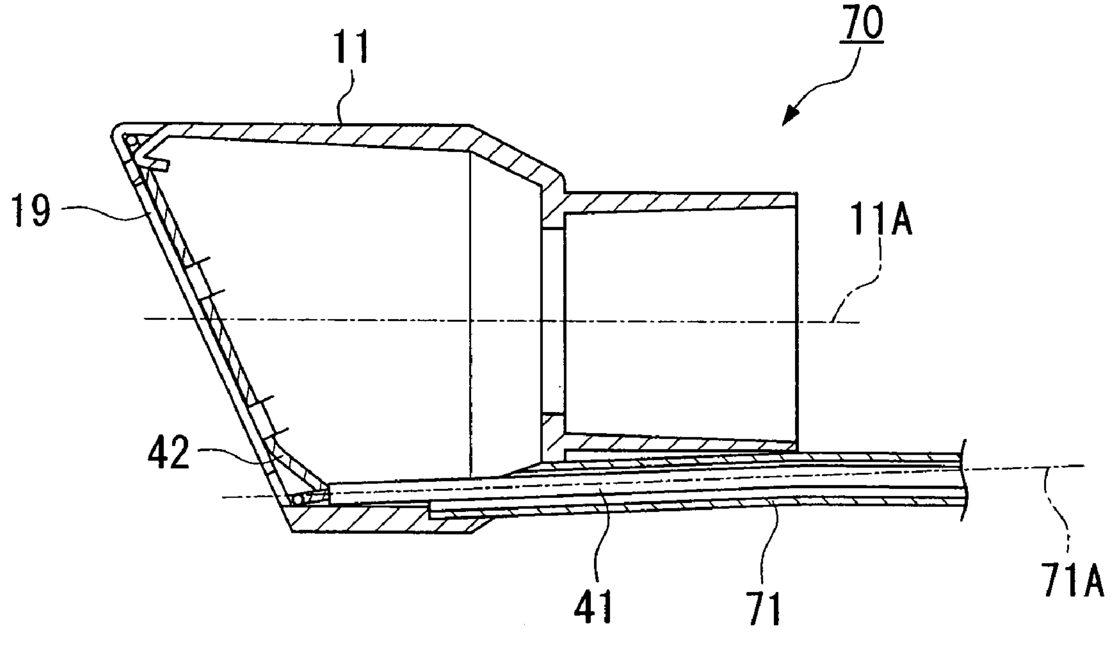
FIG. 7 is a cross section for the endoscope hood according to a third embodiment of the present invention which is viewed in an axial direction.

The third embodiment is different from the first embodiment in that the center axis 16A of the soft tube 16 in the first embodiment is parallel with the center axis 11A of the cap section 11; in contrast, a center axis 71A of the soft tube 71 near the tip as shown in FIG. 7 is disposed in a slanted manner toward an outside of a radial direction of the nail section 19 with reference to the center axis 11A of the cap section 11 in the endoscope hood 70 in the third embodiment.

The endoscope hood 70 has a similar operability and an effect which are equal to those in the endoscope hood 2 in the first embodiment. If a center axis 71A of a soft tube 71 is disposed to be separate to an outside of a radial direction of the nail section 19 with reference to the center axis 11A of the cap section 11, a section near the sheath 41 of the snare wire 42 can be engaged inside of the nail section 10 more reliably.

Figure 8:
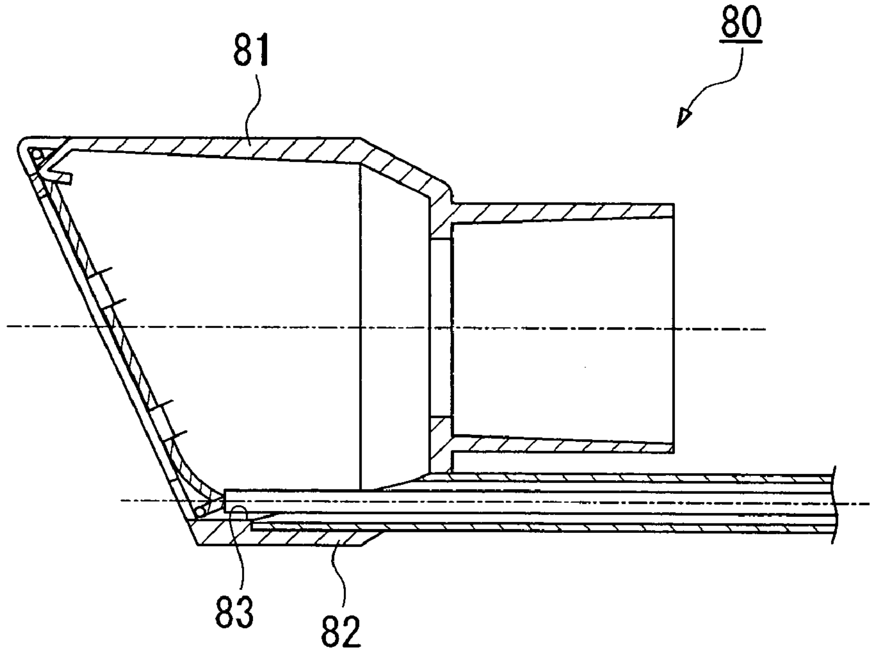
FIG. 8 is a cross section for the endoscope hood according to a fourth embodiment of the present invention which is viewed in an axial direction.
Figure 9:
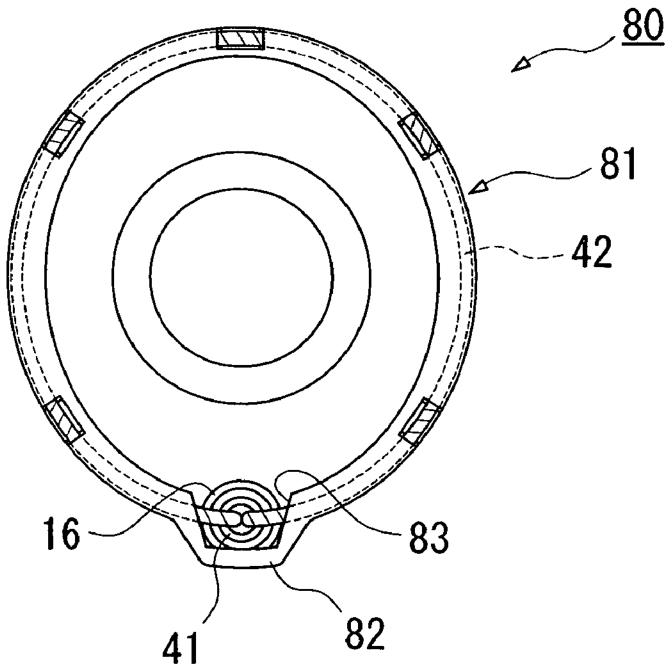
FIG. 9 is a plan view for showing a tip of a cap section in an endoscope hood according to the fourth embodiment of the present invention.
Figure 10:
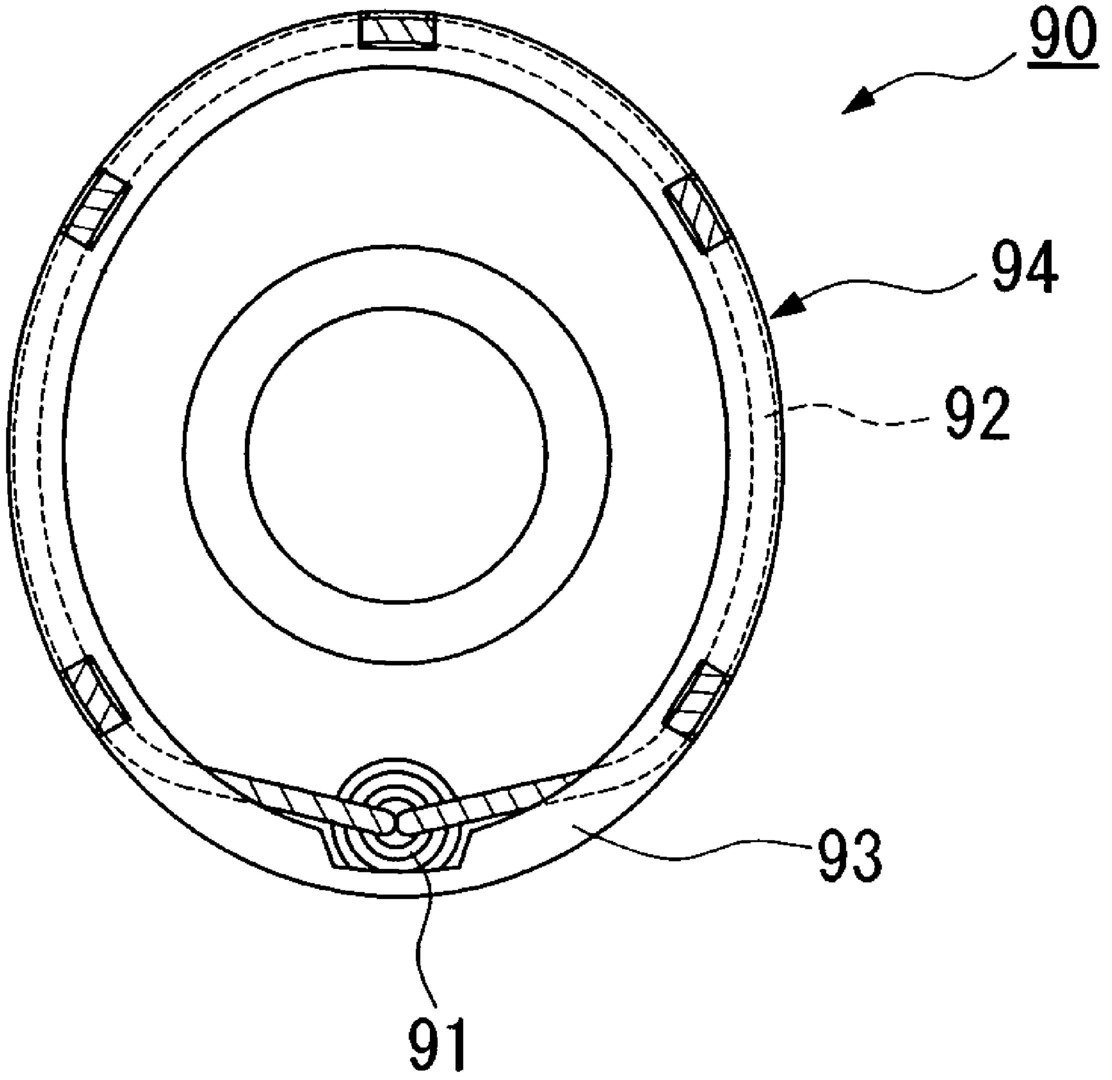
FIG. 10 is a plan view for showing a cap section of the conventional endoscope hood.

Next, a fourth embodiment is explained with reference to FIGS. 8 and 9.

Here, a basic structure in the present embodiment which is explained here is similar to the basic structure in the above explained first embodiment. In the present embodiment, other feature is added to the above explained first embodiment. Therefore, the same reference numeral are added to FIGS. 8 and 9 as the reference numeral in FIGS. 2A and 3 so as to omit the explanation therefor.

The fourth embodiment is different from the first embodiment in that the cap section 11 in the first embodiment is an approximate cylinder; in contrast, a cap section 81 has a protruding section 82 which protrudes from an outer wall and expands toward to the tip, the cap section 81 has a groove section 83 which corresponds to the protruding section 82 thereinside, and the tip of the soft tube 16 is disposed in the groove section 83.

The endoscope hood 80 has an operability and an effect which are similar to those in the eridoscope hood 2 in the first embodiment. The tip of the soft tube 16 is disposed in the groove section 83 in the endoscope hood 80; therefore, if the soft tube 16 is disposed so as to be separate toward an outside of a radial direction, a section near the sheath 41 of the snare wire 42 can be engaged inside of the nail section 19 more reliably. Also, the movement of the sheath 41 in a circumferential direction is regulated by disposing the sheath 41 in the groove 83.

Here, the present invention is not limited to the above explained embodiments. That is, it will be apparent that the invention can be embodied in a wide variety of forms, some of which may be quite different from those of the disclosed embodiments unless departing from the spirit and scope of the present invention.

For example, in the above embodiments, although the tip of the cap section is formed in a slanted manner with reference to a center axis of the cap section, it is acceptable if the tip of the cap section may be formed by an orthogonal surface with reference to the center axis.

According to the present invention, it is possible to form an endoscopic mucosa cutting device in which a possibility for a fall-off of the snare wire from the flange section is restricted if a force is applied to the cap section externally.

According to the present invention, if the cap is deformed by an external force when the snare wire of the high frequency snare is spread in the cap section so as to be disposed inside of the flange section, a possibility of a removal of the snare wire from the flange section can be restricted. Therefore, it is possible to perform an endoscopic demucosation in a stable condition.

According to the present invention, the width of the flange section is formed so as to increase toward the snare feeding section; therefore, it is possible to form the snare wire feeding section more largely; thus, it is possible to engage the snare wire near the snare sheath inside of the flange section.

According to the present invention, the width of the flange section is formed so as to increase toward the snare feeding section; therefore, it is possible to form the snare wire feeding section more largely; thus, it is possible to engage the snare wire near the snare sheath inside of the flange section more reliably.

According to the present invention, the center axis of the cap section is disposed in a slanted manner toward outside of a radial direction of the flange section; therefore, the snare wire which is fed from the snare sheath is disposed in an outer margin of the flange section which is disposed in an outer-side of the radial direction of the flange section so as to be engaged there more reliably.

According to the present invention, the tip of the soft tube is disposed in the groove which corresponds to the spiral protruding section; therefore, it is possible to dispose the soft tube outer-side of the radial direction. Therefore, it is possible to dispose the snare wire which is fed from the snare sheath which exists in the soft tube in outer-side of the radial direction of the flange section.

According to the present invention, it is possible to support the snare wire by the flange section and the flexible stopping section more reliably; thus, a possibility of a fall-off therefrom can be restricted.

What is claimed is:

1. An endoscope hood comprising:

a cylindrical cap section having a flange section proturding toward an inside of an inner surface of a tip margin of the cylindrical cap section;

an attaching section disposed between a base terminal of the cylindrical cap section and a tip of an inserting section of the endoscope;

a soft tube disposed outside of the inserting section of the endoscope, through which a high frequency snare sheath having a snare wire is inserted, an aperture of the tip reaching an inside of the cylindrical cap section, the high frequency snare sheath being inserted in the soft tube and reaching the inside of the cylindrical cap section; and a snare-wire-feeding section having a notch disposed in a corresponding position to the aperture of the tip of the soft tube, the snare-wire-feeding section being formed on the flange section; wherein the snare wire of the high frequency snare sheath can be disposed inside of the flange section by spreading the snare wire of the high frequency snare sheath in the cap section;

and, a center axis of the soft tube is disposed so that the fed snare wire passes through the snare-wire-feeding section, wherein the center axis of the soft tube nearer to the tip of the soft tube is disposed in a slanted manner toward an outside of a radial direction of the flange section with reference to a center axis of the cap section.

2. An endoscope hood comprising:

a cylindrical cap section having a flange section protruding toward an inside of an inner surface of a tip margin of the cylindrical cap section;

an attaching section disposed between a base terminal of the cap section and a tip of an inserting section of the endoscope;

a soft tube disposed outside of the inserting section of the endoscope through which a high frequency snare sheath having a snare wire is inserted, an aperture of the tip reaching the inside of the cylindrical cap section, a high frequency snare sheath being inserted in the soft tube and reaching the inside of the cap section; and a snare-wire-feeding section having a notch disposed in a corresponding position to the aperture of the tip of the soft tube, the snare-wire-feeding section being formed on the flange section; wherein the snare wire of the high frequency snare sheath can be disposed inside of the flange section by spreading the snare wire of the high frequency snare sheath in the cylindrical cap section;

and, a center axis of the high frequency snare sheath inserted in the soft tube is disposed so that the aperture of the soft tube of the fed snare wire passes through the snare-wire-feeding section, wherein the center axis of the soft tube nearer to the tip of the soft tube is disposed in a slanted manner toward an outside of a radial direction of the flange section with reference to a center axis of the cap section.

3. An endoscope hood according to claim 1, wherein a width of the flange section increases toward the snare-wire-feeding section.

4. An endoscope hood according to the claim 1, wherein:

the cap section has a protruding section which protrudes from an outer wall so as to extend toward the tip;

the cap section has a groove section in the cap section so as to correspond to the protruding section; and the tip of the soft tube is disposed in the groove section.

5. An endoscope hood according to claim 3 which is formed unitarily with the cap section by a slit which is formed near a tip margin of the flange section and the cap section in at least a part of the near section of the tip margin of the cap section and has a flexible stopping section for supporting the snare wire together with the flange section in an inside of the cap section.

* * * * *